United States Patent [19]
Risteli et al.

[11] Patent Number: 6,093,803
[45] Date of Patent: Jul. 25, 2000

[54] METHOD OF PRODUCING AMINOTERMINAL PROPEPTIDE OF TYPE 1 PROCOLLAGEN

[75] Inventors: Juha Risteli; Leila Risteli; Jukka Melkko; Saila Kauppila, all of Oulu, Finland

[73] Assignee: Orion-Yhtyma Oy, Finland

[21] Appl. No.: 09/033,310

[22] Filed: Mar. 2, 1998

Related U.S. Application Data

[62] Division of application No. 08/480,822, Jun. 7, 1995, Pat. No. 5,895,746.

[30] Foreign Application Priority Data

Apr. 19, 1995 [GB] United Kingdom .................. 9507985

[51] Int. Cl.$^7$ .............................. C07K 1/16; C07K 1/20; C07K 14/78
[52] U.S. Cl. ........................ 530/412; 530/416; 530/417; 530/300; 530/350; 530/356
[58] Field of Search .................... 530/412, 413, 530/416, 417, 414, 415, 422, 300, 350, 356

[56] References Cited

U.S. PATENT DOCUMENTS 5,698,407  12/1997  Risteli et al. ............................ 435/7.9

FOREIGN PATENT DOCUMENTS 0304292  2/1994  European Pat. Off. .

OTHER PUBLICATIONS

Oikarinen, A. et al. A new method to mesure type I and III collagen synthesis in human skin in vivo: demonstration of decreased collagen synthesis after topical glucocorticoid treatment. J. Invest. Dermatol. 98: 220–225, 1992.

Haapasaari, K–M. et al. Recovery of human skin collagen synthesis after short–term topical coricosteroid treatment and comprison between young and old subjects. Br. J. Dermatol., 135: 65–69, 1996.

Uitto, J. Collagen polymorphism: isolation and partial characterization of alpha 1(1)–trimer molecules in normal human skin. Arch. Biochem. Biophys., 192(2): 371–379, 1979.

Franks, F. Characterization of Proteins. Humana Press, Clifton, New Jersey, Chapter 4, pp. 95–125, 1988.

Ebeling, Peter R., et al., "Utility of Type I Procollagen Propeptide Assays for Assessing Abnormalities in Metabolic Bone Diseases", Journal of Bone and Mineral Research, vol. 7, No. 11, pp. 1243–1250 (1992).

Jukkola, Arja, et al., "Procollagen Synthesis and Extracellular Matrix Deposition in MG–63 Osteosarcoma Cells", Journal of Bone and Mineral Research, vol. 8, No. 6, pp. 651–657 (1993).

Kohler, G., et al., "Continuous cultures of fused cells secreting antibody of predefined specificity", Nature, vol. 256, pp. 495–497 (1975).

Linkhart, Susan G., et al., "Synthetic Peptide–Based Immunoassay for Amino–Terminal Propeptide of Type I Procollagen: Application for Evaluation of Bone Formation", Clin. Chem., vol. 39, No. 11, pp. 2254–2258 (1993).

Mellko, Jukka et al., "Radioimmunoassay of the Carboxyterminal Propeptide of Human Type I Procollagen", Clin. Chem., vol. 36, No. 7, pp. 1328–1332 (1990).

Price, Karen M., et al., "Development of a radioimmunoassay for fetal antigen 2", Clin. Chem. Acta., vol. 224, pp. 95–102 (1994).

Skerra, Arne, et al., "Assembly of a Functional Immunoglobulin $F_v$ Fragment in *Escherichia coli*", Science, vol. 240, pp. 1038–1041 (1988).

Teisner, B., et al., "Fetal antigen 2: An amniotic protein identified as the aminopropeptide of the α 1 chain of human procollagen type I", APMIS, vol. 100, pp. 1106–1114 (1992).

Frei et al., Hepatology, vol. 4, pp. 830–834 (1984).

Rohde et al., Fresenius Z., Anal. Chem. vol. 290, pp. 151–152 (1978).

Mellko et al., Clin. Chem., vol. 36, No. 7, pp. 1326–1332 (1990).

Taubman et al., Science, vol. 186, pp. 1115–1117 (1974).

Pesciotta et al., Biochemistry, vol. 19, pp. 2447–2454 (1980).

Foellmer et al., Eur. J. Biochem., vol. 134, pp. 183–189 (1983).

*Primary Examiner*—Nancy A. Johnson
*Assistant Examiner*—Anne L. Holleran
*Attorney, Agent, or Firm*—Baker Botts

[57] ABSTRACT

Aminoterminal propeptide of type I procollagen exists in serum in two forms: classical type I procollagen which is a heterotrimer containing two pro α1-chains and one pro α2-chain of type I procollagen, and an α1-homotrimer type I procollagen containing three identical pro α1-chains. These intact, trimeric aminoterminal propeptides may be isolated without the use of proteolytic enzymes and the resultant propeptides may be used to prepare antibodies specific for the intact trimeric propeptide, having no affinity for the monomeric form of the propeptide. Such antibodies are useful in methods of assaying intact trimeric aminoterminal propeptide of type I procollagen in serum, without false information resulting from inadvertent assay of the monomeric form of the propeptide.

6 Claims, 1 Drawing Sheet

METHOD OF PRODUCING AMINOTERMINAL PROPEPTIDE OF TYPE 1 PROCOLLAGEN

This application is a divisional application of U.S. Ser. No. 08/480,822, filed Jun. 7, 1995, now U.S. Pat. No. 5,895,746 which is incorporated by reference herein.

BACKGROUND OF THE INVENTION

The present invention relates to an improved assay method for the immunological determination of intact, either classical or α1-homotrimer, aminoterminal propeptide of type I procollagen in a sample such as serum, and to preparation of an antiserum suitable for use in this method.

Type I collagen is the most abundant collagen type in the human body. Most of it is found in the bones, although other soft connective tissues also contain considerable amounts of it. In mineralized tissues such as bone, about 90% of the organic matrix is type I collagen, there being no other collagen types in these tissues. Thus analysis of type I collagen is important in diseases affecting bones, such as metabolic bone diseases including primary and secondary osteoporosis, bone metastases in breast or prostatic carcinomas, rheumatoid arthritis and various genetic diseases such as osteogenesis imperfecta. It is also known that the collagen synthesis rate in bone affected by various hormones, e.g. growth hormone, thyroxine, cortisol and estrogens.

Type I collagen is synthesized as a procollagen, containing propeptide extensions at both ends of the molecule. The rate of type I collagen synthesis can thus be assessed by determining the amount of propeptide liberated during the conversion of procollagen to collagen. It is known to assay the carboxyterminal propeptide of type I procollagen (abbreviated PICP) in serum (Melkko J, Niemi S, Risteli L, Risteli J: Clin. Chem. 1990; 36; 1328–1332). However, there are certain individuals in whom the elimination rate of this propeptide from the circulation is deteriorated, leading to very high serum levels of PICP, which are not related to the rate of synthesis of type I procollagen. On the other hand, the previous assays developed for the aminoterminal propeptide of type I procollagen have been based either on synthetic monomeric linear peptides (Ebeling P R, Peterson J M, Riggs B L; J. Bone Miner. Res. 1992; 7; 1243–1250 and Linkhart S G, Linkhart T A, Taylor A D, Wergedahl J E, Bettica P, Baylink D J: Clin. Chem. 1993; 39; 2254–2258) or on propeptides quasi isolated from amniotic fluid (Teisner B, Boje Rasmussen H, Hoejrup P, Yde-Anderson E, Skjoedt K: APMIS 1992; 100; 1106–1114 and Price K M, Silman R, Armstrong P, Grudzinskas JG: Clin. Chim Acta 1994; 224; 95–102) or cell culture medium (Jukkola A, Risteli L, Melkko J. Risteli J: J. Bone Miner. Res. 1993; 8; 651–657). Such assays have been found to detect two antigenic forms in human serum, are of different sizes. One of the forms corresponds to the authentic trimeric propeptide in size and the other is its further degradation product, which resembles the globular, so called Col1 domain of the propeptide.

The evidence available suggests that these small molecular weight degradation products are not derived from the further degradation of the liberated propeptide but most likely from the degradation of type I procollagen molecules that have retained the aminoterminal propeptide in the tissues (so called pN type I collagen). Such molecules are found on the surface of type I collagen fibers, mainly in soft connective tissues and temporarily in newly synthesised non-mineralized osteoid. Further, it has been shown that the authentic aminoterminal propeptide is eliminated from the circulation via the scavenger-receptor of the liver endothelial cells, whereas the smaller Col1 related degradation products are eliminated via the kidneys. Thus kidney disease, while decreasing the clearance of the Col 1-related peptide, would greatly affect the serum concentration of such peptides and give false results with respect to collagen synthesis. Since the intact aminoterminal propeptides of type I procollagen are not excreted into the urine, the assay of the present invention is applicable to serum and other biological fluids except urine. In addition, the catabolic status often encountered in seriously ill patients will increase the tissue degradation of pN type I collagen, similarly increasing the serum Col1 concentration and giving false information on the anabolic capacity of the patient.

It would, therefore, be desirable to solve the interpretation problem of the results caused by the different origins and elimination routes of the two propeptide forms and to provide a quantitative method, which is quick and simple to practise, for assaying only the intact aminoterminal propeptide of type I procollagen in human serum, to the exclusion of the Col 1-related degradation products.

The intact propeptide is in the form of a trimer, whereas the degradation product comprises the monomeric globular Col1 domain of the α1-chain of type I procollagen. When isolating the intact, trimeric aminoterminal propeptide of type I procollagen from pleural fluid from a carcinoma patient, two separate propeptides were surprisingly discovered, which differed with respect to their constituent chains. Two different polypeptide chains were found in the propeptide form eluting first from the DEAE-chromatography column, since the classical type I procollagen is a heterotrimer containing two pro α1-chains and one pro α2-chain of type I procollagen. The more acidic propeptide lacked the second polypeptide chain that moves faster in electrophoresis and is known to be derived from the pro α2-chain of type I procollagen. This atypical propeptide was derived from the α1-homotrimer type I procollagen containing three identical pro α1-chains. Such a collagen has been previously described in a fully processed form from the tissues of patients with certain disease states e.g. breast, lung and stomach carcinomas, but the corresponding propeptides have not been identified. Since the aminoterminal portion of the pro α2-chain is truncated with respect to the pro α1-chain and lacks the whole of the Col1 domain, the α1-homotrimer propeptide has three Col1 domains and the classical propeptide only two. Since the Col1 domains are phosphorylated, these two intact propeptides can be separated from each other on the basis of the difference in their charge, e.g. using DEAE-chromatography at pH 5.0. Since the α1-homotrimer propeptide has three Col1 domains and the classical propeptide only two, the latter elutes earlier in anion-exchange chromatography. Both these propeptides are susceptible to being denatured at low pH (less than 5.0); something which is not easily detected but can cause problems when producing antibodies if proper precautions are not taken.

The antisera used previously for assaying the aminoterminal propeptide of type I procollagen has affinity not only for the intact trimeric propeptide, but to a considerable extent also for the monomeric form. This is due to the nature of the antigen used to raise the antisera. When a linear synthetic peptide, or a propeptide derived from amniotic fluid and isolated in a monomeric form, is used for raising the antibodies, these antibodies react preferentially with the monomeric Col1 degradation products. On the other hand, when the propeptide is isolated from cell culture fluid, it is first purified in the form of a procollagen, which is later digested by bacterial collagenase to liberate the propeptide from the collagen proper. Since the authentic propeptide still contains a collagenous domain, part of the bacterial collagenase binds to it, but is not able to digest the propeptide during the short in vitro incubation and isolating procedures. Consequently, when such a propeptide is used as an immunogen, the enzyme is capable of functioning, leading to in vivo degradation of the propeptide and production of antibodies towards its degradation products. In addition, it is also necessary to avoid such conditions and methods (e.g. high performance liquid chromatography at pH lower than 5.0) which would denature even a small portion of the propeptide during the isolation procedure of the aminoterminal propeptide of type I procollagen. This is beacuse, in contrast to the corresponding propeptide of type III procollagen (EP-B-0-304292), the aminoterminal of type I procollagen has no interchain disulphide bonds, which would stabilize the structure and facilitate rapid renaturation after minor accidental denaturation during the purification procedure. Thus, removal of contaminating enzymes from type III procollagen can be effected by reverse phase separation at low pH. This would, however, lead to denaturation of trimeric PINP of type I procollagen because of its lack of stabilising disulphide bonds.

SUMMARY OF THE INVENTION

Accordingly, starting materials for methods of the invention are preferably free from such contaminating proteolytic enzymes.

The present invention provides intact, trimeric classical aminoterminal propeptide of type I procollagen and intact trimeric α1-homotrimer aminoterminal propeptide of type I procollagen, these propeptides having been isolated without the use of a proteolytic enzyme. Thus the isolated propeptides are free from enzymes such as bacterial collagenase, which are capable of degrading the propeptide to its monomeric form. The propeptides of the invention may be labelled, using any suitable label. Examples of suitable labels include radiolabels, biotin (which may be detected by avidin or streptavidin conjugated to peroxidase), lanthanides, alkaline phosphatase and fluorescent labels (e.g. fluorescein and rhodamine).

The present invention also provides a purification procedure for the intact classical and α1-homotrimer aminoterminal propeptides of human type I procollagen. It also provides an antibody raised against either of the two forms of the intact propeptide, preferably against the α1-homotrimer form, which antibody has little or no affinity, preferably no affinity for the monomeric form of the propeptide. It has been discovered that the α1-homotrimer propeptide in particular provides a suitable three dimensional conformation, which is capable of raising antibodies that recognise only the correct spatial configuration found in intact propeptides, and not in the monomeric chains.

The present invention also provides a purification procedure for the intact classical and α1-homotrimer aminoterminal propeptides of human type I procollagen. As a starting material a biological source e.g. human pleural, ascitic or amniotic fluid containing said propeptides in sufficient amounts can be used. The α1-homotrimer propeptide has been found very often in malignant pleural fluid, seldom in ascitic fluid and so far not in amniotic fluid. In addition, during the isolation procedure, no active proteolytic enzymes which can partially degrade the propeptides should be present. For example, human amniotic fluid, full-term in particular, and many malignant ascitic fluids have been found to yield crude propeptide preparations which fall apart to monomeric form during isolation. This can be shown by repeated gel filtration analysis, where a previously trimeric propeptide is in later analysis split into two peaks corresponding to the authentic propeptide and its monomeric Col1 domain. The preferred isolation procedure is in essence as follows. Albumin, the contaminating protein present in the greatest amount is removed. This may be done by any suitable means e.g. by precipitating the propeptide with ammonium sulphate (saturation less than 50%, preferably 40%). This removes albumin because albumin is not precipitated. The propeptide-containing material is further purified by a first DEAE chromatographic step, preferably at a neutral pH such as from pH 6.5 to pH 7.5 e.g. pH 7.4; a gel filtration step; a second DEAE chromatographic step, preferably at low pH, such as from pH 4.8 to pH 5.2 e.g. pH 5.0, and reverse phase separation, preferably at a neutral pH such as pH 6.5 to pH 7.5, particularly pH 7.4.

Since the propeptides are acidic due to phosphorylation of certain serine residues, they will bind tightly to a DEAE column over a wide pH range (from 5.0 to 8.5) and elute in a sharp peak with NaCl. During the first DEAE chromatography step, a neutral pH is preferable in order to keep the large amounts of other contaminating proteins in solution. This enables effective separation of the propeptides of interest. Subsequent gel filtration removes proteins larger and smaller than the propeptides. The column can be developed with various buffers, e.g. with 0.2M ammonium bicarbonate, pH 7.9, which has the advantage that it can later be removed by lyophilization. The second DEAE chromatography step at low pH (e.g. about 5.0) removes remnants of proteins which were not totally separated previously due to the large amount of material present. Final purification is obtained with reverse phase separation, which should be performed at neutral pH, such as from pH 6.5 to 7.5, e.g. 7.4, to preserve the native trimeric conformation of the propeptide. A widely used reverse phase separation in 0.1% TFA as a mobile phase leads to low yield of propeptides due to partial denaturation and problems in obtaining trimer specific antibodies. Example 1 describes in detail how the propeptides can be isolated from malignant pleural fluid.

The invention also provides an antibody that is specific for intact, heterotrimeric classical aminoterminal propeptide of type I procollagen, or for intact trimeric α-1 homotrimer aminoterminal propeptide of type I procollagen; which antibody does not specifically bind to the monomeric form of said propeptide. Thus, antibodies of the invention have little or no affinity, preferably no affinity, for the monomeric form of the propeptide, but binds to one or both of the trimeric forms. The antibody has utility in detecting and quantitatively determining human PINP, and hence is useful in diagnosis of diseases and conditions associated with abnormal levels of PINP such as the diseases and conditions listed hereinabove.

The antibody is preferably monoclonal, but may also be polyclonal. The antibody may be labelled. Examples of suitable antibody labels include radiolabels, biotin (which may be detected by avidin or streptavidin conjugated to peroxidase), lanthanides, alkaline phosphatase and fluorescent labels (e.g. fluorescein and rhodamine). The term "antibody" is used herein to include both complete antibody molecules and fragments thereof. Preferred fragments contain at least one antigen binding site, such as Fab and F(ab')2 fragments. Humanised antibodies and fragments thereof are also included within the term "antibody".

The antibody is produced by raising antibodies in a host animal against an aminoterminal propeptide according to the invention or against an antigenic epitope thereof (hereinafter "the immunogen"). The epitope will, of course, be representative of the intact trimeric form of the propeptide i.e. an antibody to the epitope will not recognise the monomeric form of the propeptide. Typically therefore, such an epitope comprises two or more short amino acid sequences from different chains which are close to each other because of the configuration of the trimeric propeptide, i.e. a discontinuous rather than a continuous epitope. This configuration will not exist in the monomeric form of the peptide so antibodies to such epitopes will not recognise the monomer. Typically, antibodies of the invention are directed against the most aminoterminal non-collagenous, globular domain of PINP. The classical form of PINP is a heterotrimer containing chains derived from both the pro-α1- and the pro-α-2-chains of type I procollagen. The pro α-2-chain is truncated at the aminoterminus and does not contain the globular antibody formation inducing domain. To distinguish the trimeric and monomeric forms of the propeptide, the antibodies must react with the three-dimensional conformation and not with an individual chain. Thus, the α-1 homotrimer PINP, which contains three similar chains all having this globular domain is particularly suitable for raising antibodies of the invention that recognise a feature of the propeptides' conformation containing three or two different chains in the correct conformation are involved in the antigenic determinant. Such antibodies can not be formed when linear synthetic peptides or monomeric chains are used as immunogens.

Methods of producing monoclonal and polyclonal antibodies are well-known in the art and any of these methods may be used to prepare antibodies according to the invention. A method for producing a polyclonal antibody comprises immunising a suitable host animal, for example an experimental animal, with the immunogen and using properly diluted serum or isolating immunoglobulins from the serum. The animal may therefore be inoculated with the immunogen, with blood subsequently being removed from the animal and the IgG fraction being purified. Methods for producing a monoclonal antibody typically comprise immortalising cells which produce the desired antibody. Hybridoma cells may be produced by fusing spleen cells from an inoculated experimental animal with tumour cells (Kohler and Milstein, Nature 256, 495–497, (1975)). The antibody may also be produced by recombinant DNA technology, for example as described by Skerra et al (1988) (Science 240, 1038–1041).

An immortalised cell producing the desired antibody may be selected by a conventional procedure. The hybridomas may be grown in culture or injected intraperitoneally for formation of ascites fluid or into the bloodstream of an allogenic host or immunocompromised host. Human antibodies may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, chicken, sheep, guinea pig, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified, for example to a purity of up to 70%, up to 80%, up to 90% up to 95%, up to 99% or up to 100%.

The present invention also provides a method of assaying the intact aminoterminal propeptide of type I procollagen, which method comprises contacting a sample to be assayed with an antibody of the invention in the presence of a label, such that the label is bound to the propeptide/antibody complex formed, and assaying the amount of bound and/or unbound label.

In principle, any assay technique that allows detection, and preferably quantification, of either the classical heterotrimeric propeptide or the α1 homotrimer, and which relies on specific binding to one of these peptides by an antibody of the invention, may be employed. One preferred type of method relies on the use of labelled antibodies, preferably radiolabelled antibodies. In such methods, the amount of (labelled) propeptide (antigen)/antibody complex is assayed, thus giving a measure of the amount of propeptide (antigen) in the sample.

Another preferred type of method relies on the use of labelled antigen (intact trimeric propeptide in either the classical or α1 homotrimeric type) together with an antibody of the invention. In such methods, a known amount of labelled, preferably radiolabelled, antigen is added to a sample containing an unkown amount of unlabelled propeptide (antigen). Both the labelled and the unlabelled antigen bind to the antibody, for example in a competitive manner and an assay of the amount of bound labelled propeptide compared to the known amount added can be used to determine how much unlabelled antigen is present in the sample. Methods of these preferred types are described in more detail below.

If the α1-homotrimer propeptide is to be assayed, the sample must be treated, e.g. by DEAE chromatography, prior to the assay, in order to separate the classical and α1-homotrimer propeptides and labelled α1-homotrimer propeptide used as tracer, since the assay itself does not distinguish between these two propeptide forms.

The invention provides a method of detecting and/or quantitatively determining in a sample intact, trimeric human PINP which method comprises:

(a) contacting the sample with an antibody of the invention, for example labelled antibody such as a radiolabelled antibody; and (b) detecting and/or quantitatively determining the binding of the antibody to either of the intact trimeric forms of PINP.

More particularly, the invention provides a method for assaying intact, trimeric, aminoterminal propeptide of human type I procollagen, which method comprises contacting in any order: (i) a sample of a human body fluid, which sample is known or suspected to contain such propeptide; (ii) an antibody which specifically binds to intact, trimeric propeptide of human type I procollagen but not to said propeptide when it is in monomeric form; and (iii) a known amount of labelled trimeric propeptide of the invention, which acts as an antigen, such that the label is bound to the antibody in an amount which depends on the amount of unlabelled propeptide present in the sample; and assaying the amount of the bound and/or unbound label as a measure of unlabelled the level of intact, trimeric aminoterminal propeptide of human type I procollagen in the sample.

The human body fluid may be, for example, blood, plasma, serum, healing wound fluid, ascitic fluid, cerebral fluid, pleural fluid, synovial fluid, suction blister fluid of skin or amniotic fluid.

A method for detecting or quantitatively determining intact, trimeric human PINP is Western blotting. Such a method can comprise the steps of:

(i) subjecting a sample containing or suspected of containing a target intact, trimeric human PINP to gel electrophoresis to separate the peptides in the sample;

(ii) transferring the separated peptides onto a solid support (e.g. a nitrocellulose support) by blotting; and (iii) allowing a labelled antibody according to the invention to bind to the target intact, trimeric human PINP.

Methods of quantitative determination include ELISA (enzyme-linked immunoassay) methods such as ELISA methods or a radioimmunoassay method. Typically, an ELISA method comprises the steps of:

(i) immobilising on a solid support an unlabelled antibody according to the invention;

(ii) adding a sample containing or suspected of containing the target intact, trimeric, human PINP such that the PINP is captured by the unlabelled antibody;

(iii) adding a labelled antibody according to the invention; and (iv) quantitatively determining the amount of bound labelled antibody.

Typically a radioimmunoassay method comprises the steps of:

(i) contacting a sample containing or suspected of containing the propeptide to be detected with a first antibody according to the invention and a labelled, preferably radiolabelled, propeptide of the invention;

(ii) contacting the resulting material with an immobilised second antibody which binds to the first antibody;

(iii) separating out the immobilised material from the non-immobilised material; and (iv) comparing the radioactivity of the immobilised or non-immobilised material with the activity obtained using samples of known concentration of propeptide to determine the concentration of propeptide in the sample being assayed.

The present invention also provides a kit suitable for carrying out an assay method of the invention. The kit may comprise an antibody, for example a labelled antibody, as described above specific for intact trimeric aminoterminal propeptide of type I procollagen which has little or no affinity, preferably no affinity, for the monomeric form of the propeptide. Alternatively, the kit may comprise an antibody of the invention and a labelled, preferably radiolabelled, propeptide of the invention which acts as an antigen and enables the amount of unlabelled antigen in the sample to be determined.

DETAILED DESCRIPTION OF THE PREFERRED EMBODIMENTS

Figure 1:
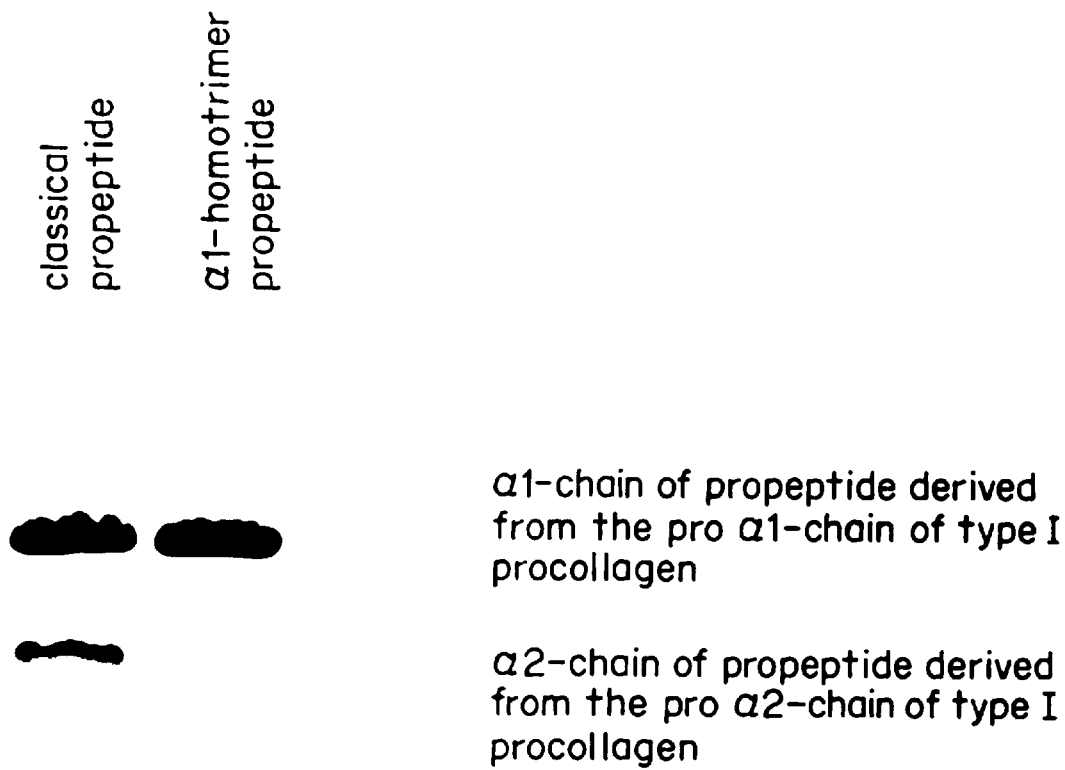
FIG. 1 is an electrophoretic gel of purified classical and α1-homotrimeric aminoterminal propeptides of human type I procollagen isolated from human pleural fluid.

The following examples illustrate and further explain the invention.

EXAMPLE 1

Isolation of the Intact Classical and α1-homotrimer Aminoterminal Propeptides of Human Type I Procollagen in Native Conformation without using Proteolytic Enzymes.

Five to ten liters of human pleural fluid removed from lung cancer patients for palliative reasons are precipitated with solid $(NH_4)_2SO_4$ (40% saturation) in the presence of protease inhibitors (3 milligrams/liter of phenylmethylsulfonyl fluid, N-ethylmaleimide and p-hydroxymercuribenzoate and 10 mM EDTA). The precipitated proteins are collected by centrifugation at 15000×g for 30 min and dissolved in 50 mM Tris/HCl, pH 7.4, containing the above protease inhibitors, and are dialysed against this buffer. The sample is then chromatographed on a DEAE-Sephacel column (5×50 cm) equilibrated in this buffer. Elution is carried out with a linear gradient of NaCl (0 to 0.5 M NaCl, 4000+4000 ml). The intact classical and α1-homotrimer aminoterminal propeptides of human type I collagen are eluted late in the gradient, after the bulk of other proteins. When using an immunoassay detecting both the monomeric and trimeric propeptides, the minor amount of the monomeric Col1-related peptides are eluted first, then the intact classical propeptide, and finally the α1-homotrimer aminoterminal propeptide of human type I procollagen. The fractions containing the two propeptides are pooled separately and purified independently, applying the procedure described below. The pools are dialysed against 0.2M $NH_4HCO_3$, pH 7.9, and lyophilized. The samples are dissolved in 0.2M $NH_4HCO_3$, and subjected to chromatography on a Sephacryl S-300 column (1.5×110 cm) equilibrated in this solution. The fractions containing the propeptide antigenicity (between the elution positions of human IgG and Albumin) are pooled and lyophilized. The samples are then dissolved in 50 mM ammonium acetate buffer, pH 5.0, briefly dialzyed against it and subjected to chromatography on an anion-exchange column (Protein-Pak DEAE-5P) using a high performance liquid chromatography (HPLC) instrument. The propeptides are eluted using a linear gradient of NaCl (0 to 0.3 M, 0 to 60 min, flow rate 1 ml/min). Final purification of the propeptide is performed using HPLC by directly injecting the fractions containing the propeptide into a pH stable reverse phase column (Vydac, Hesperia, Calif.) in 0.4% ammonium acetate, pH 7.4, and eluting the bound propeptide with increasing concentrations of acetonitrile (0 to 70%, 0 to 45 min). The propeptide is eluted as a sharp peak in the first half of the gradient, located by immunoassay, pooled and lyophilized. The purity of the classical and α1-homotrimer aminoterminal propeptides of human type I procollagen isolated from human pleural fluid are shown in FIG. 1 using SDS-polyacrylamide gel electrophoresis (Separating gel 15%). As type I procollagen contains no interchain disulphide bonds, the constituent chains are dissociated by this procedure.

In contrast to the aminoterminal propeptide of type III procollagen (PIIINP) neither the classical nor the α1 homotrimeric form of the PINP propeptide contains interchain disulphide bonds, which in PIIINP covalently link the three constituent chains together. Thus the individual chains of the PINP fall apart in sodium-dodecyl-sulphate (SDS) slab-gel electrophoresis (FIG. 1) and the trimeric structure can not be verified. The isolated classical and α1-homotrimer propeptides are trimeric, however, since only one immunoreactive peak corresponding to the size of the authentic propeptide is found in size exclusion chromatography and no reaction is observed at the elution position of the degradation products of the propeptide. When propeptides after storage in frozen state were repeatedly analysed by gel filtration no degradation to smaller forms was observed.

EXAMPLE 2

Antiserum Production.

Polyclonal antibodies against PINP were raised in New Zealand White rabbits by intradermal injections of 150 μg/rabbit of highly purified α1-homotrimer PINP (free of proteolytic enzymes), dissolved in 1 ml of 0.9% NaCl and mixed with an equal volume of complete Freund's adjuvant. Several booster injections (75 μg/rabbit of α1-homotrimer PINP in 1 ml of 0.9% NaCl and mixed with an equal volume of incomplete Freund's adjuvant) were given at three-week-intervals. The antiserum pool was made for each rabbit from several bleedings.

EXAMPLE 3

Performance of the Equilibrium Type of Radio-imunoassay.

Ten micrograms of the classical (or α1-homotrimer) aminoterminal propeptide of type I procollagen is labelled with 1 millicurie of $^{125}$iodine by Chloramine-T (10 micrograms) and the labelled propeptide is separated from free iodine by gel filtration on a Sephacryl S-300 column (1×20 cm) equilibrated in PBS-buffer containing bovine serum albumin (1 gram/liter). The labelled propeptide is eluted from the column as a sharp peak well before the free iodine. Antiserum binding curves are prepared with 50000 counts per minute of the labelled propeptide. The propeptide concentration in an unknown sample of serum, or other biological fluid except urine is determined in the following radioimmunoinhibition assay. A pretested diluted antiserum (200 μl) is incubated with the unknown sample (50 μl) and 50000 counts per minute of the tracer (in 200 μl of PBS-buffer containing 1 gram/liter of bovine serum albumin) for 2 hours at 37° C. Then a solid phase second antibody against rabbit gamma globulin is added and after 20 min incubation at 20° C. the antigen bound in the immunocomplex is separated by centrifugation (2000×g for 20 min) from the solution. The inhibition activity of the unknown sample is compared with the activity of standard concentrations of unlabelled aminoterminal propeptide of type I procollagen.

EXAMPLE 4

Separation of the Classical and α1-homotrimer Aminoterminal Propeptides of Type I Procollagen from Each Other in a Sample Prior to Radioimunoassay.

If the sample, either serum or other biological fluid except urine, contains both the classical and α1-homotrimer aminoterminal propeptides of type I procollagen, these can be separated by chromatography on an anion-exchange column (Protein-Pak DEAE-5P) using a high performance liquid chromatography. A one millilitre sample is dialysed against 50 mM ammonium acetate buffer, pH 5.0, injected into the column and eluted using a linear gradient of NaCl (0 to 0.3 M, 0 to 60 min, flow rate 1 ml/min) collecting one millilitre fractions. The fractions are then analyzed by radioimmunoassay for the classical aminoterminal propeptide of type I procollagen and the presence and location of the two forms of the aminoterminal propeptides of type I procollagen are detected. If an accurate measurement of the correct amount is needed the fractions containing the said propeptides are pooled, briefly dialysed against distilled water, lyophilized and finally dissolved into PBS-buffer using the original volume of the sample and the concentrations of the propeptides are determined by radioimmunoassay for the classical aminoterminal propeptide of type I procollagen.

It is possible to measure either the α1-homotrimer or the classical heterotrimer by using the proper tracer.

What is claimed is:

1. A process for producing an intact trimeric α-1 homotrimeric aminoterminal propeptide of type 1 procollagen wherein said propeptide is isolated from a biological sample without the use of proteolytic enzymes comprising subjecting the propeptide to chromatography without denaturing the propeptide to provide at least one chromatographic fraction containing the propeptide, and recovering the propeptide from the fraction.

2. A process for producing an intact heterotrimeric aminoterminal propeptide of type I procollagen wherein said propeptide is isolated from a biological sample without the use of proteolytic enzymes comprising subjecting the propeptide to chromatography without denaturing the propeptide to provide at least one chromatographic fraction containing the propeptide, and recovering the propeptide from the fraction.

3. A process as claimed in claim 1 wherein the chromatography comprises anion-exchange purification at a pH of about 5.0 and reverse phase separation at neutral pH.

4. A process as claimed in claim 2 wherein the chromatography comprises anion-exchange purification at a pH of about 5.0 and reverse phase separation at neutral pH.

5. A process according to claim 1 wherein the chromatography comprises anion-exchange purification at a pH of about 5.0 and reverse phase separation at a pH above 5.0.

6. A process according to claim 2 wherein the chromatography comprises anion-exchange purification at a pH of about 5.0 and reverse phase separation at a pH above 5.0.

* * * * *